United States Patent [19]

Mathys

[11] Patent Number: 5,142,911

[45] Date of Patent: Sep. 1, 1992

[54] DEVICE FOR MEASURING THE STRENGTH OF PIECES OF COMPRESSED MOLDING MATERIAL

[75] Inventor: Ernst Mathys, Schaffhausen, Switzerland

[73] Assignee: Georg Fischer AG, Schaffhausen, Switzerland

[21] Appl. No.: 681,939

[22] Filed: Apr. 8, 1991

[30] Foreign Application Priority Data

Apr. 6, 1990 [CH] Switzerland ............... 01184/90-4

[51] Int. Cl.$^5$ .............................................. G01N 3/48
[52] U.S. Cl. ........................................... 73/573; 73/81
[58] Field of Search ................. 73/862.59, 821, 573, 73/575, 818, 661, 449, 454, 81

[56] References Cited

U.S. PATENT DOCUMENTS

| | | | |
|---|---|---|---|
| 3,472,063 | 10/1969 | Branson | 73/573 |
| 3,955,404 | 5/1976 | Bickel et al. | 73/573 |
| 4,827,771 | 5/1989 | Cary et al. | 73/644 |

FOREIGN PATENT DOCUMENTS 3404922 9/1987 Fed. Rep. of Germany .
3720625 1/1989 Fed. Rep. of Germany .

Primary Examiner—Jerry W. Myracle
Attorney, Agent, or Firm—Anderson, Kill, Oshinsky

[57] ABSTRACT

A device for measuring the strength of pieces of compressed molding material. The device includes a probe pin and a stop surface arranged on the housing. On the end of the housing opposite the probe pin is arranged a cover for replacing batteries arranged within the housing. When the probe pin is inserted into the compressed molding material, a digital display indicates the resistance to insertion measured by a crystal unit converted as molding material strengths in N/cm$^2$ or PSI.

6 Claims, 1 Drawing Sheet

DEVICE FOR MEASURING THE STRENGTH OF PIECES OF COMPRESSED MOLDING MATERIAL

BACKGROUND OF THE INVENTION

1. Field of the Invention

The present invention relates to a device for measuring the strength of pieces of compressed molding material, such as, casting molds or test pieces. The device includes a probe pin which is insertable into the piece of molding material. The probe pin is connected to a force sensor for measuring the resistance of insertion of the probe pin. The device further includes a digital display for the measured value and a current source.

2. Description of the Related Art

A device of the above-described type is known from DE-C-3404922. This known device consists of a pick-up component and a device component, so that two hands are necessary for operating the device. The force sensor is a resistance strain gauge which requires a preamplifier and 9-volt batteries as the current source.

Thus, the known device is very complicated and its manufacture is expensive and cumbersome.

SUMMARY OF THE INVENTION

Therefore, it is the object of the present invention to provide a device of the above-described type which is inexpensive to manufacture due to a small number of components and which can be operated by means of one hand because of its small dimensions.

In accordance with the present invention, the force sensor is a crystal unit which is connected to the digital display through a frequency measuring logic and microprocessor. The device further includes a housing which contains all the components of the device and the digital display. The device can be operated with one hand.

Because of the use of a crystal unit as the force sensor and a microprocessor, amplifiers are unnecessary and it is possible to use current sources with low voltage and, therefore, the device is simple and small, so that it can be operated with one hand.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

DESCRIPTION OF THE PREFERRED EMBODIMENT

Figure 1:
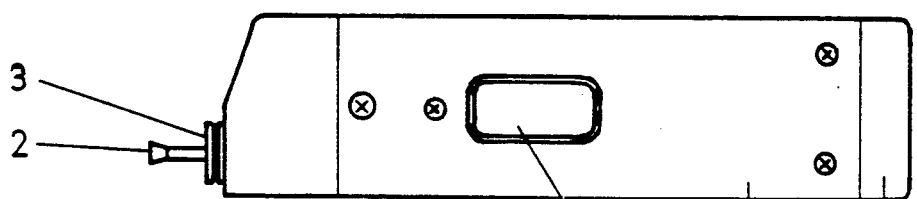
FIG. 1 is a top view of the device according to the present invention.
Figure 2:
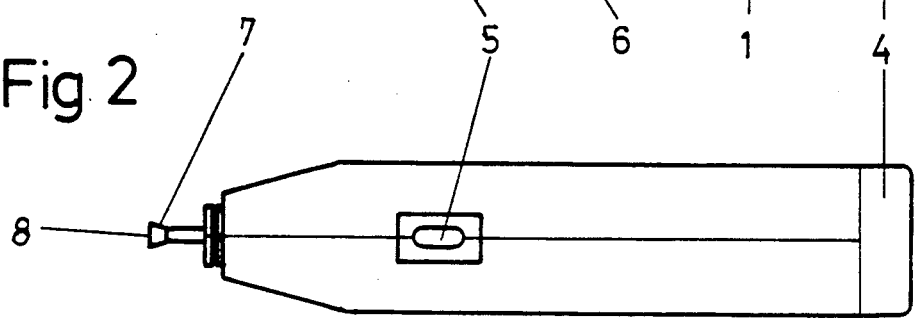
FIG. 2 is a side view of the device of FIG. 1.

As shown in FIGS. 1 and 2, the device according to the present invention includes a probe pin 2 and a stop surface 3 arranged at a front end of a housing 1. A removable cover 4 is arranged at the other end of the housing 1. After removal of cover 4, batteries are accessible and can be removed.

Figure 3:
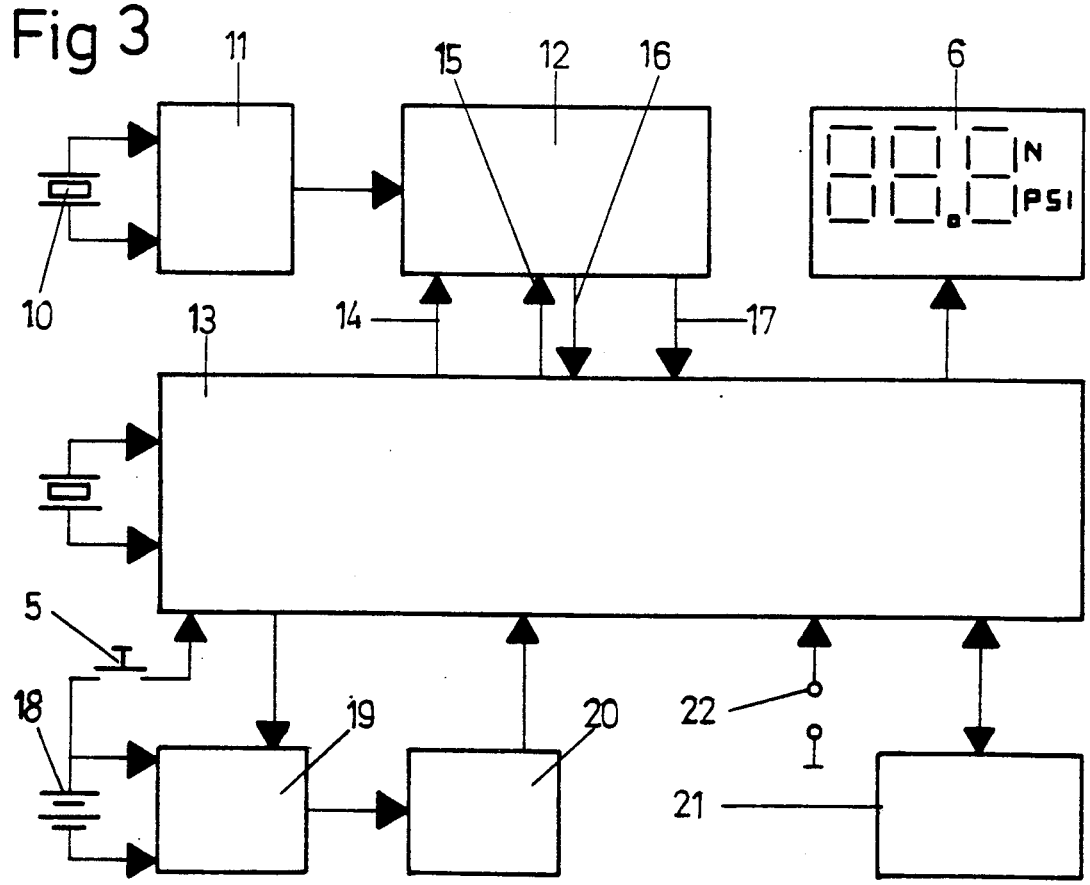
FIG. 3 a block diagram of the device.

The probe pin 1 acts on a force sensor 10 which is schematically shown in FIG. 3. The force sensor 10 is constructed as a crystal unit or oscillator crystal.

A control button 5 for switching on the device is arranged on a longitudinal side of the housing 1. A digital display 6 is arranged on the other longitudinal side of the housing 1.

Control button 5 and digital display 6 are arranged on housing 1 relative to each other in such a way that, when the device is held in one hand, the control button 5 can be operated with a finger and the digital display 6 is visible without obstruction.

The measured values of the compressive strength of the piece of molding material are displayed on the digital display 6 in $N/cm^2$ or, after switching by means of control button 5, in PSI.

The probe pin 2 is shaped so as to conically widen toward the insertion end 7 and has a plane end surface 8.

As can be seen in the block diagram of FIG. 3, the force sensor 10 constructed as crystal unit or oscillator crystal is connected through a generator 11 to a frequency measuring logic 12.

The frequency measuring logic 12 is connected to a microprocessor 13 through a connection 14 for starting time measurement, a connection 15 for time base, a connection 16 for f-cycle and a connection 17 for end measurement.

A current source 18 in the form of a battery is connected to the microprocessor through the control button 5, on the one hand, and through a starting logic 75 and a reset logic 20, on the other hand.

A fixed value storage 21 for the reference value and the last measurement as well as reference value adjuster 22 are also connected to the microprocessor 13.

The measured values of the resistance to penetration when the probe pin 2 is inserted into the piece of molding material up to the stop 3 are converted in the microprocessor 13 into compressive strength values of the compacted material up to the stop 3 and are indicated on the digital display 6 $N/cm^2$ or PSI.

Because of its small dimensions, the device according to the invention can be used in the automatic manufacturing of molds for measuring the mold strength at different or critical locations. The measured values are indicated or stored in central processing locations. The measured values can also be used automatically for controlling the mold compression in a certain range.

While a specific embodiment of the invention has been shown and described in detail to illustrate the application of the inventive principle, it will be understood that the invention may be embodied otherwise without departing from such principles.

I claim:
1. In a device for measuring the strength of pieces of compressed molding material, the device including a stop surface and a probe pin insertable into the piece of molding material up to the stop surface, the probe pin being connected to a force sensor for measuring the resistance to insertion in the piece of molding material, a digital display for the measured value and current source, the improvement comprising the force sensor being a crystal unit, a frequency measuring logic and a microprocessor connecting the crystal unit to the digital display, and a housing containing all components of the device and the digital display, wherein the device is configured to be usable with one hand.

2. The device according to claim 1, comprising a control button for switching the digital display for the measured resistance converted to compressive strength between $N/cm^2$ and PSI.

3. The device according to claim 1, comprising batteries as the current source, and a removable cover for the batteries.

4. The device according to claim 1, comprising two 1.5-volt batteries as the current source.

5. The device according to claim 1, wherein the housing is of plastics material.

6. A device for measuring the strength of pieces of compressed molding material, the device comprising a housing of plastics material, a stop surface provided on the housing and a probe pin insertable into the piece of molding material until the piece of molding material contacts the stop surface, the probe pin being connected to a force sensor for measuring the resistance to insertion in the piece of molding material, a digital display for the measured value and current source, the force sensor being a crystal unit, a frequency measuring logic and a microprocessor connecting the crystal unit to the digital display, a control button for switching the digital display for the measured distance converted to compressive strengths between $N/cm^2$ and PSI, and batteries as the current source, and a removable cover for the batteries, wherein the housing contains all components of the device and the digital display, and wherein the device is configured to be usable with one hand.

* * * * *